United States Patent
Hegazi et al.

(10) Patent No.: US 10,281,448 B2
(45) Date of Patent: May 7, 2019

(54) DETERMINING THE DETERIORATION OF OILS USING FLUORESCENCE RISE-TIME

(71) Applicant: Saudi Arabian Oil Company, Dhahran (SA)

(72) Inventors: Ezzat Hegazi, Dhahran (SA); Vincent Cunningham, Dhahran (SA); Maha Nour, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 357 days.

(21) Appl. No.: 15/248,578

(22) Filed: Aug. 26, 2016

(65) Prior Publication Data

US 2017/0205387 A1 Jul. 20, 2017

Related U.S. Application Data

(60) Provisional application No. 62/280,439, filed on Jan. 19, 2016.

(51) Int. Cl.
| | |
|---|---|
| *G01N 11/00* | (2006.01) |
| *G01N 11/12* | (2006.01) |
| *G01N 21/64* | (2006.01) |
| *G01N 33/28* | (2006.01) |

(52) U.S. Cl.
CPC ............. *G01N 33/28* (2013.01); *G01N 11/00* (2013.01); *G01N 11/12* (2013.01); *G01N 21/64* (2013.01); *G01N 21/6408* (2013.01); *G01N 33/2888* (2013.01); *G01N 2011/008* (2013.01)

(58) Field of Classification Search
None
See application file for complete search history.

(56) References Cited

U.S. PATENT DOCUMENTS

| | | | |
|---|---|---|---|
| 5,158,720 | A | 10/1992 | Levy |
| 6,255,118 | B1 | 7/2001 | Alfano et al. |
| 6,633,043 | B2 | 10/2003 | Hegazi et al. |
| 6,810,718 | B2 | 11/2004 | Wilson et al. |
| 7,322,927 | B2 | 1/2008 | Buechler |
| 7,560,711 | B2 | 7/2009 | Hegazi |

(Continued)

OTHER PUBLICATIONS

Al-Sabagh, A.M., et al.; "Synthesis of polymeric additives based on itaconic acid and their evaluation as pour point depressants for lube oil in relation to rheological flow properties" Egyptian Journal of Petroleum (2012) 21; pp. 19-30.

(Continued)

*Primary Examiner* — Edwin C Gunberg
(74) *Attorney, Agent, or Firm* — Bracewell LLP; Constance G. Rhebergen; Brian H. Tompkins (57) ABSTRACT

Methods, media, and devices for determining the deterioration of an oil by determining the viscosity of the oil from fluorescence rise-time are provided. A sample of an oil from a machine may be obtained. The oil sample may be irradiated using a light source such a laser to induce fluorescence in the oil sample. The induced fluorescence may be filtered and collimated before being detecting by a photodiode. The relative intensity of the fluorescence may be measured over a time period at a sample rate and used to determine the fluorescence rise-time of the oil sample. The viscosity of the oil sample may be determined from the fluorescence rise-time. The determined viscosity may be compared to viscosity threshold value to determine the deterioration of the oil.

56 Claims, 7 Drawing Sheets

(56) References Cited

U.S. PATENT DOCUMENTS

| | | |
|---|---|---|
| 7,705,982 B2 | 4/2010 | Triana et al. |
| 8,455,845 B2 | 6/2013 | Hegazi et al. |
| 2003/0141459 A1 | 7/2003 | Hegazi et al. |
| 2007/0187617 A1 | 8/2007 | Kong et al. |
| 2013/0295567 A1 | 11/2013 | Link et al. |
| 2014/0291550 A1 | 10/2014 | Jimenez et al. |

OTHER PUBLICATIONS

Pouzar, Miloslav, et al.; "Determination of metals in lubricating oils by X-ray fluorescence spectrometry" Talanta 54 (2001); pp. 829-835.

Mu, Taotao, et al.; "Characterization of edible oils using time-resolved fluorescence" Royal Society of Chemistry, Anal. Methods, 2014, 6; pp. 940-943.

Hegazi, E. and Hamdan, A.; "Estimation of crude oil grade using time-resolved fluorescence spectra" Talanta 56 (2002); pp. 989-995.

Ryder, A.G., et al.; "Characterization of crude oils using fluorescence lifetime data" Spectrochimica Acta Part A 58 (2002); pp. 1025-1037.

Ossia, C.V., et al.; "On the use of intrinsic fluorescence emission ration in the characterization of hydraulic oil degradation" ScienceDirect Tribology International 41 (2008); pp. 103-110.

Guan, L., et al.; "Application of dielectric spectroscopy for engine lubricating oil degradation monitoring" ScienceDirect Sensors and Actuators A 168 (2011); pp. 22-29.

Rajendiran, A., et al.; "Thermal, spectral, oxidation stability and antioxidant behavior on Group II base oils" ScienceDirect Fuel 137 (2014); pp. 122-134.

Wang, Xin and Mullins, Oliver C.; "Fluorescence Lifetime Studies of Crude Oils" Applied Spectroscopy vol. 48, No. 8, 1994; pp. 977-984.

Ryder, Alan G.; "Time-Resolved Fluorescence Spectroscopic Study of Crude Petroleum Oils: Influence of Chemical Composition" Applied Spectroscopy vol. 58, No. 5, 2004; pp. 613-623.

Ralston, Corie Y., et al.; Quantum Yields of Crude Oils Applied Spectroscopy vol. 50, No. 12, 1996; pp. 1563-1568.

Hegazi, E., et al.; "New Approach for Spectral Characterization of Crude Oil Using Time-Resolved Fluorescence Spectra" Applied Spectroscopy vol. 55, No. 2, 2001; pp. 202-207.

Pantoja, Patricia A., et al.; "Prediction of Crude Oil Properties and Chemical Composition by Means of Steady-State and Time-Resolved Fluorescence" ACS Publications, Energy Fuels 2011, 25; pp. 3598-3604.

International Search Report and Written Opinion for International PCT application PCT/US2017/014091 (SA5437/PCT); International Filing Date Jan. 19, 2017; Report dated Mar. 30, 2017 (pp. 1-12).

DETERMINING THE DETERIORATION OF OILS USING FLUORESCENCE RISE-TIME

CROSS-REFERENCE TO RELATED PATENT APPLICATIONS

This application claims priority from U.S. Provisional Application No. 62/280,439, filed Jan. 19, 2016, and titled "DETERMINING THE DETERIORATION OF OILS USING FLUORESCENCE RISE-TIME." For purposes of United States patent practice, this application incorporates the contents of the Provisional Application by reference in its entirety.

BACKGROUND

Field of the Disclosure

Embodiments of the disclosure generally relate to methods, computer-readable media, systems, and devices for determining the deterioration of machine lubrication oils. More specifically, the present disclosure relates to determining the viscosity of a lubrication oil.

Description of the Related Art

Machines, such as gas turbines, may employ oil as a lubricant during operation. Lubrication oils may be used to reduce friction between components of the machine and minimize or prevent wear of such components over time. Lubrication oils, especially those used in gas turbines, may deteriorate while in use due to various factors, such as oxidization due to air exposure, depletion of additives such as anti-oxidants and demulsifiers, and chemical deformation of the oil itself due to high temperatures. The deterioration of lubrication oils may lead to the creation of insoluble compounds which eventually break off from the oil and become deposited in the machine. Additionally, some machines, such as gas turbines, are subject to contamination with materials such as water, metal deposits, and other substances, such as add-on chemicals.

Existing tests to monitor the lifetime of a lubrication oil may include directly determining the viscosity by measuring the time for the oil to flow under gravity through a calibrated glass capillary viscometer. Other tests used to monitor the lifetime of a lubrication oil may include determining the total acid number of the oil and the oxidation stability of the oil. These and other existing tests may be time-consuming and expensive, and may require testing of the oil offsite. Other tests used on lubrication oil may determine the water content, the existence of metals and other particles; however, such tests measure the contamination of the lubrication oil but fail to measure the deterioration of the lubrication oil itself.

SUMMARY

Embodiments of the disclosure generally related to methods, computer-readable media, and devices for determining the deterioration of oils by determining a viscosity from a fluorescence rise-time associated with a sample of the oil. In some embodiments, a method for determining the deterioration of an oil is provided that includes determining a fluorescence rise-time of an oil sample from two or more measurements of induced fluorescence in the oil sample. The oil sample may be a sample of an oil from a machine. The method further includes determining the viscosity of the oil from the fluorescence rise-time and comparing the viscosity to a viscosity threshold. Finally the method includes determining deterioration of the oil based on the comparison.

Additionally, in some embodiments the method includes emitting light from a light source into the oil sample to induce fluorescence in the oil sample and measuring, over a time period, the intensity of the detected fluorescence at a sample rate to obtain the two or more measurements. In some embodiments, the light source is a laser. In some embodiments, the laser emits light at a wavelength of about 405 nanometers (nm). In some embodiments the sample rate is 20 milliseconds (ms). In some embodiments, measuring, over a time period, the intensity of the detected fluorescence at a sample rate to obtain the two or more measurements includes measuring the intensity of the detected fluorescence using a photodiode. In some embodiments, the method includes filtering the induced fluorescence before measuring, over a time period, the intensity of the detected fluorescence at a sample rate to obtain the two or more measurements and collimating the induced fluorescence before measuring, over a time period, the intensity of the detected fluorescence at a sample rate to obtain the two or more measurements. In some embodiments, determining deterioration of the oil based on the comparison includes determining that the oil is deteriorated if the viscosity deviates from the viscosity threshold by a predetermined amount or by a predetermined percentage. In some embodiments, the method includes providing a notification on a display of a viscosity determination device indicating the oil has deteriorated. In some embodiments, the machine is a gas turbine and the oil is a gas turbine oil. In some embodiments, the method includes obtaining the oil sample from the machine. In some embodiments, obtaining the oil sample includes depositing the oil sample in a glass cuvette. In some embodiments, the method includes providing a notification on a display of a viscosity determination device if the viscosity deviates from the viscosity threshold by a predetermined amount or a predetermined percentage. In some embodiments, determining the viscosity of the oil from the fluorescence rise-time includes determining the viscosity according to Equation 1:

$$\text{Viscosity} = \frac{\ln(Risetime) - B}{A} \qquad (1)$$

Additionally, in some embodiments a non-transitory computer-readable storage medium having executable code stored on the medium for determining deterioration of an oil is provided. The executable code includes a set of instructions that causes a viscosity processor to perform the operations including determining a fluorescence rise-time of an oil sample from two or more measurements of induced fluorescence in the oil sample, the oil sample includes a sample of an oil from a machine and determining the viscosity of the oil from the fluorescence rise-time. The operations further include comparing the viscosity to a viscosity threshold and determining deterioration of the oil based on the comparison.

In some embodiments, the operations include controlling a laser to emit light from a light source into the oil sample to induce fluorescence in the oil sample and receiving, over a time period, measurements of the intensity of the detected fluorescence by a detector at a sample rate to obtain the two or more measurements. In some embodiments, the detector is a photodiode. In some embodiments, the operations include providing, on a display coupled to the viscosity processor, a notification indicating the oil has deteriorated.

In some embodiments, a portable viscosity determination device is provided. The device includes a housing and a light source disposed in the housing and arranged to emit light into an oil sample contained in a sample container. The oil sample includes a sample of an oil from a machine. The portable viscosity determination device further includes a viscosity processor disposed in the housing and a non-transitory computer-readable memory disposed in the housing, the memory having executable code stored on the memory. The executable code includes a set of instructions that causes a viscosity processor to perform operations including determining a fluorescence rise-time of the oil sample from two or more measurements of fluorescence induced by the light source in the oil sample and determining the viscosity of the oil from the fluorescence rise-time.

In some embodiments, the operations include comparing the viscosity to a viscosity threshold and determining deterioration of the oil based on the comparison. In some embodiments, the operations include providing, on a display coupled to the viscosity processor, a notification indicating the oil has deteriorated. In some embodiments, the operations include providing a notification, on a display coupled to the viscosity processor if the viscosity deviates from the viscosity threshold by a predetermined amount or a predetermined percentage. In some embodiments, the portable viscosity determination device includes a detector arranged to detect the induced fluorescence. In some embodiments, the detector is arranged at a 90° angel from a surface of the sample container. In some embodiments, the operations include controlling the light source to emit light into the oil sample to induce fluorescence in the oil sample and receiving, over a time period, measurements of the intensity of the induced fluorescence by the detector at a sample rate to obtain the two or more measurements. In some embodiments, the detector is a photodiode. In some embodiments, the portable viscosity determination device includes a filter disposed in the housing and arranged to filter the induced fluorescence before detection of the induced fluorescence by the detector. Additionally, in some embodiments, the portable viscosity determination device includes a lens disposed in the housing and arranged to collimate the induced fluorescence before detection of the induced fluorescence by the detector. In some embodiments, the portable viscosity determination device includes a power source disposed in the housing and configured to provide power to the light source, the viscosity processor, and the memory. In some embodiments, the portable viscosity determination device includes a display disposed in the housing and coupled to the processor. In some embodiments, the light source is arranged to irradiate the oil sample in the sample container at about a 45° angle from a surface of the oil sample. The portable viscosity determination device includes the sample container. In some embodiments, the sample container is removably attached to the housing.

In some embodiments, a method for determining the viscosity of an oil is provided. The method includes emitting light from a light source into a sample of the oil to induce fluorescence in the oil sample and measuring, over a time period, the intensity of the induced fluorescence at a sample rate to obtain two or more measurements. The method further includes determining a fluorescence rise-time of the oil from the two or more measurements of induced fluorescence in the oil sample and determining the viscosity of the oil from the fluorescence rise-time.

In some embodiments, a non-transitory computer-readable storage medium having executable code stored on the medium for determining the viscosity an oil. The executable code includes a set of instructions that causes a viscosity processor to perform operations including emitting light from a light source into a sample of the oil to induce fluorescence in the oil sample and measuring, over a time period, the intensity of the induced fluorescence at a sample rate to obtain two or more measurements. The operations also include determining a fluorescence rise-time of the oil from the two or more measurements of induced fluorescence in the oil sample and determining the viscosity of the oil from the fluorescence rise-time.

Moreover, in some embodiments, a system for determining the viscosity of an oil is provided. The system includes a viscosity processor and a non-transitory computer-readable memory, the memory having executable code stored on the medium. The executable code includes a set of instructions that causes a viscosity processor to perform operations including emitting light from a light source into a sample of the oil to induce fluorescence in the oil sample and measuring, over a time period, the intensity of the induced fluorescence at a sample rate to obtain two or more measurements. The operations further include determining a fluorescence rise-time of the oil from the two or more measurements of induced fluorescence in the oil sample and determining the viscosity of the oil from the fluorescence rise-time.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments set forth in the disclosure. Rather, these embodiments are provided so that this disclosure will be thorough and complete, and will fully convey the scope of the disclosure to those skilled in the art.

Embodiments of the disclosure include systems, devices, computer-readable media, and methods for determining the viscosity of a lubrication oil from the induced fluorescence rise-time of the oil. As described infra, the rate of change of the induced fluorescence intensity, as represented by the fluorescence rise-time, directly correlates with the viscosity of the lubrication oil. As used in the disclosure, a lubrication oil may include, for example, an engine oil, a motor oil, a gear oil, a turbine oil, or other oils used in machines. Machines using such oils may include gas turbines, steam turbines, engines, and other machines.

In some embodiments, fluorescence may be induced in a lubrication oil sample via a light source such as a pulsed laser. The induced fluorescence may be detected over a time period, and the relative intensity of the induced fluorescence may be measured at a sample rate over the time period. The fluorescence rise-time of the lubrication oil sample may be determined from the measured relative intensities. The viscosity of the lubrication oil sample may then be determined from the fluorescence rise-time. In some embodiments, the viscosity may be compared to a threshold viscosity value to determine deterioration of the sampled lubrication oil.

In some embodiments, a lubrication oil sample may be obtained from a machine and positioned in a viscosity determination system or device such as a portable viscosity determination device for determining viscosity from fluorescence rise-time. In some embodiments, the lubrication oil sample may be obtained onsite at the location of the machine, such as by obtaining lubrication oil from a gas turbine at a gas turbine plant. Using the viscosity determination system or device, fluorescence may be induced in the lubrication oil sample and the induced fluorescence may be detected, and the intensity of the induced fluorescence may be measured. The fluorescence measurements may be provided over a time period to a viscosity determination processor that may determine a fluorescence rise-time and determine a viscosity from the fluorescence rise-time. In some embodiments, the fluorescence rise-time may be compared to a threshold viscosity value. If the viscosity deviates from the threshold viscosity value by a specific amount or percentage, the deterioration of the sampled lubrication oil may be determined to be unacceptable. In such embodiments, if the deterioration of the sampled lubrication is determined to be unacceptable, a notification may be provided, such as a visual notification (for example, an alert or alarm) on a display of the viscosity determination device. If the deterioration of the sampled lubrication oil is determined to be acceptable, the determined viscosity may or may not be provided to a display.

Experiment Setup

Figure 1:
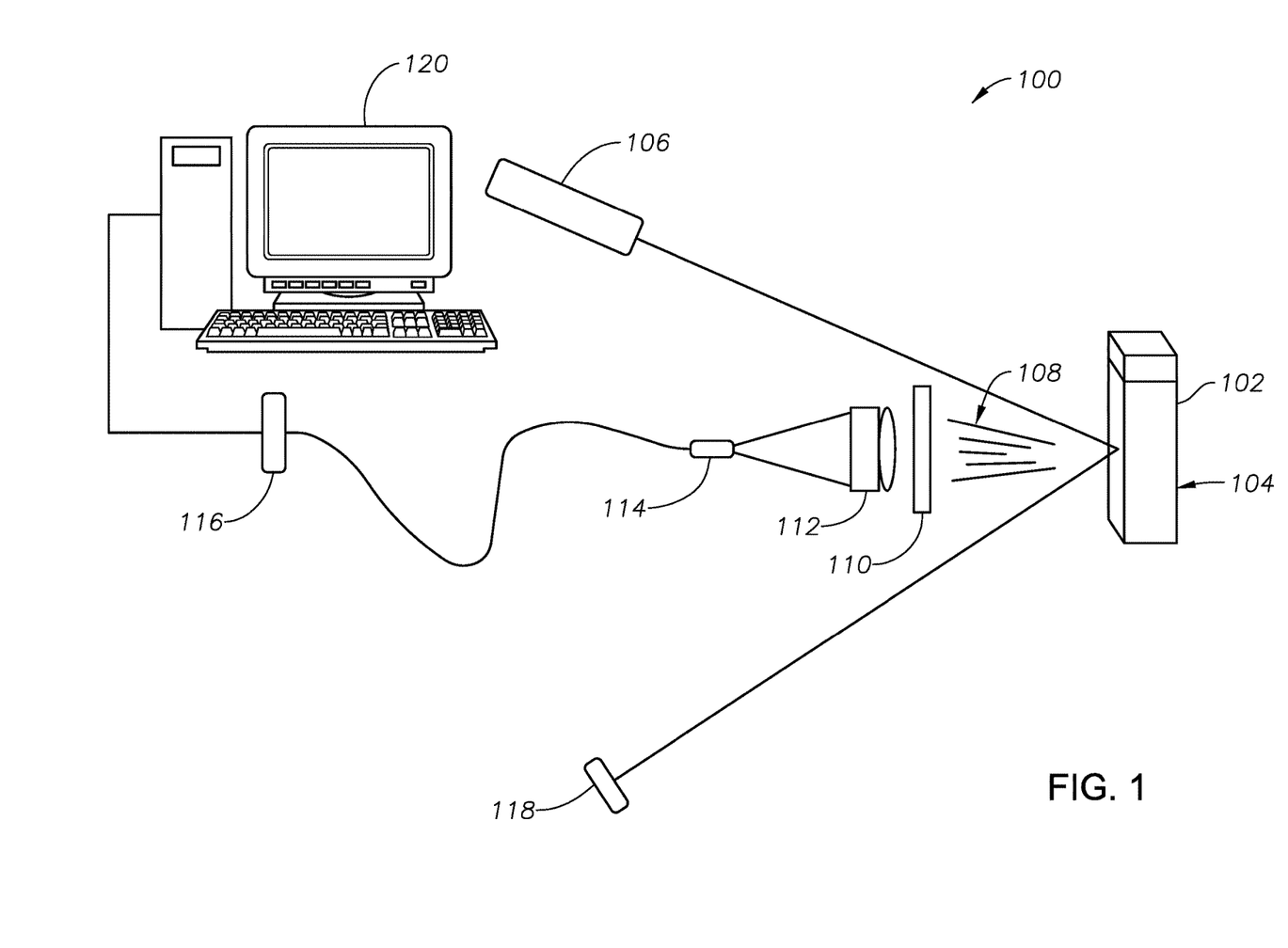
FIG. 1 is a schematic diagram of an a system for determining fluorescence rise-time of an oil sample in accordance with an embodiment of the disclosure.

FIG. 1 depicts a system 100 for measuring fluorescence rise-time of an oil sample in accordance with an embodiment of the disclosure. The system 100 may include, for example, a cuvette 102 containing an oil sample 104, a pulsed laser 106, an optical filter 110, a lens 112, a fiber optic collector 114, a photodiode 116, a beam dump 118 and a computer 120. In addition to being used to obtain the experimental data described infra, it should be appreciated that, in some embodiments, the system 100 may be illustrative of a system that implements the techniques of the disclosure described in the disclosure. For example, a lubrication oil sample may be collected from a machine and transported to a location having the system 100 for determination of a viscosity.

The cuvette 102 may contain a lubrication sample for fluorescence inducement and measurement by the system 100. In some embodiments, the cuvette 102 may be a glass or transparent material cuvette having a rectangular shape. The oil sample 104 may be of sufficient volume to occupy a portion of the cuvette 102 such that the oil sample volume is suitable for inducement by the pulsed laser 106. For example, in some embodiments the oil sample 104 may be collected directly in the cuvette 102 from a machine using a lubrication oil.

The pulsed laser 106 may be positioned to irradiate the cuvette 102 at 45° from a front surface of the cuvette 102. In some embodiments, the pulsed laser 106 may have a wavelength of 405 nm, a pulse width of about 5 nanoseconds (ns), and an energy per pulse of about 2 millijoules (mJ). In some embodiments, the pulsed laser and the wavelength, pulse width, and energy per pulse of the laser may be selected based on the type (for example, composition, or viscosity grade) of the lubrication oil to be measured. In other embodiments, however, the pulsed laser 106 may have other wavelengths from about 350 nm to about 550 nm. In such embodiments, a laser wavelength may be selected based on minimization of the signal-to-noise ratio associated with the induced fluorescence.

In some embodiments, the optical filter 110 is positioned to filter fluorescence induced in the oil sample 104 and transmitted through the cuvette 102. In some embodiments, the optical filter 110 may be a narrow bandpass optical filter at 440±10 nanometers (nm). The optical filter 110 may be a glass filter or a plastic filter and, in some embodiments, may be a tunable filter. In some embodiments, the optical filter 110 may be selected based on the pulsed laser used in the system 100, the type (for example, composition, viscosity grade, etc.) of the lubrication oil to be measured, or both. The lens 112 may be a collimated lens arranged to collimate fluorescent light filtered by the optical filter 110. The fiber optic collector is positioned to collect the collimated light and transmit the collimated light to the photodiode 116.

The pulsed laser 106 may be activated to irradiate the oil sample 104 in the cuvette 102 and induce fluorescence in the oil sample 104. The fluorescence may be induced at only one wavelength (for example, 405 nm). The laser-induced fluorescence 108 from the oil sample 104 may be filtered by the optical filter 110, collimated by the collimated lens 112, and then collected by the fiber optic collector 114. The photodiode 116 may detect the laser-induced fluorescence transmitted by the fiber optic collector 114 and output a digital signal to the computer 120. Reflected and unabsorbed light from the pulsed laser 106 may be absorbed by a beam dump 118.

As described infra, the system 100 was used in a determination of viscosity from fluorescence rise-time for five oil samples. Table 1 shows the kinematic viscosity and density for the selected five oil samples obtained from new gas turbine oils and used gas turbine oils. The kinematic viscosity was measured at 20° C. using ASTM D-7042, 2004, "Standard Test Method for Dynamic Viscosity and Density of Liquids by Stabinger Viscometer (and the Calculation of Kinematic Viscosity)," ASTM International, West Conshohocken, Pa., 2004, DOI: 10.1520/D7042-04. The density was measured at 20° C. using ASTM D-4052, 2009, "Standard Test Method for Density, Relative Density, and API Gravity of Liquids by Digital Density Meter," ASTM International, West Conshohocken, Pa., 2009, DOI: 10.1520/D4052-09:

TABLE 1

Density and kinematic viscosity of oil samples

| Oil Sample | Density at 20° C. | Kinematic Viscosity at 20° C. |
|---|---|---|
| Sample 1 | 0.8739 | 31.476 |
| Sample 2 | 0.8716 | 32.605 |
| Sample 3 | 0.8723 | 32.850 |
| Sample 4 | 0.8739 | 33.084 |
| Sample 5 | 0.8739 | 33.122 |

Table 2 shows other measurements for the oil samples Sample 1, Sample 2, and Sample 4. The other measurements include total acid number (TAN) in milligrams of potassium hydroxide per gram (mg KOH/gm) and pH using ASTM D664, oxidation stability by rotary pressure vessel (RBOT) using ASTM D2272, color using ASTM D1500, and appearance using SOP 087:

TABLE 2 total acid number (TAN), pH, oxidation stability, color and appearance of oil samples

| Oil Sample | TAN (mg KOH/gm) | pH | RBOT (minutes) | Color | Appearance |
|---|---|---|---|---|---|
| Sample 1 | 0.09 | 7.1 | 514 | 0.5 | 1.2 |
| Sample 2 | 0.19 | 3.9 | 62 | 6.0 | 1.1 |
| Sample 4 | 0.10 | 6.5 | 139 | 6.0 | 1.1 |

As shown in Table 2, the additional measurements of total acid number (TAN) and pH, oxidation stability by rotary pressure vessel (RBOT), color, and appearance do not exhibit a relationship with each other or to the deterioration condition of the gas turbine oil samples.

Figure 2:
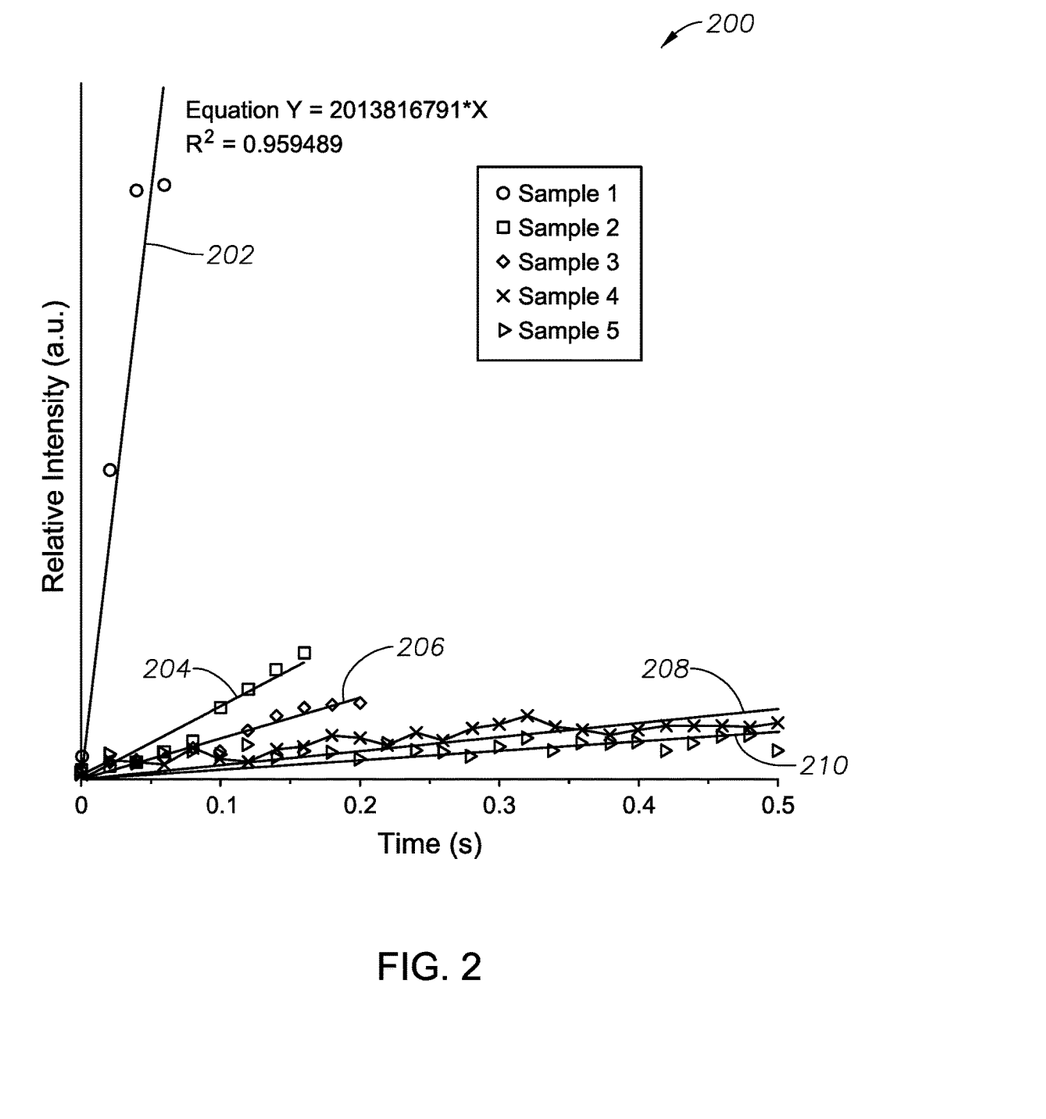
FIG. 2 is a plot of measured relative fluorescence intensity vs. time for oil samples measured using the system of FIG. 1.

With the foregoing in mind, the system 100 was used to measure the induced fluorescence of the five oil samples and determine the initial rise-time of the measured fluorescence signals. The initial rise-time was measured at an emission spectrum wavelength for the first 5 seconds at intervals of 0.02 seconds (20 milliseconds (ms)) for each sample. Accordingly, FIG. 2 depicts a plot 200 of the measured relative fluorescence intensity (in fluorescence arbitrary units (a.u.)) vs. time (in seconds(s)) for each sample. Additionally, as shown in FIG. 2, for each sample, the relative fluorescence intensity measurements are fitted to a straight line (defined by Y=Slope*X) and a value for the straight line slope is calculated for each sample. For example, as shown in FIG. 2, the fitted line 202 corresponds to Sample 1, the fitted line 204 corresponds to Sample 2, the fitted line 206 corresponds to Sample 3, the fitted line 208 corresponds to Sample 4, and the fitted line 210 corresponds to Sample 5. The slopes of each fitted line and the coefficients of determination ($R^2$) are summarized in Table 3:

TABLE 3

Slope and coefficients of determination

| Oil Sample | Slope | Coefficients of determination ($R^2$) |
|---|---|---|
| Sample 1 | 2.013816791 | 0.959489 |
| Sample 2 | 0.1247684162 | 0.974061 |
| Sample 3 | 0.07010516072 | 0.980222 |
| Sample 4 | 0.03239473034 | 0.952228 |
| Sample 5 | 0..01932770101 | 0.848357 |

As shown in Table 3, the coefficients of determination for the fitted lines of Sample 1, Sample 2, Sample 3, and Sample 4 are all greater than 95%. The coefficients of determination for Sample 5 were influenced by a relatively weak fluorescence signal-to-noise ratio at the 20 ms sampling time.

Figure 3:
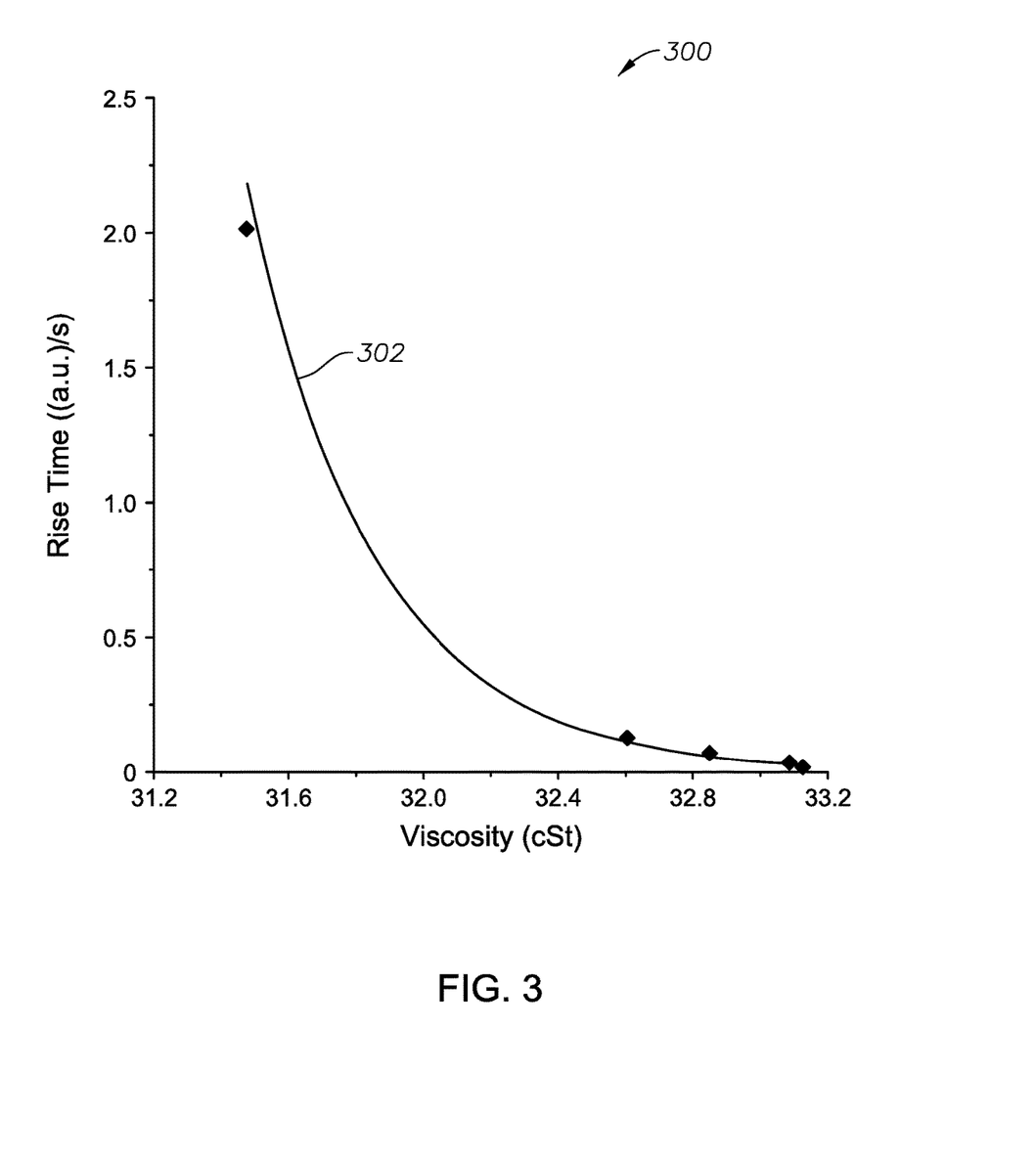
FIG. 3 is a plot of the slopes of the fitted lines shown in FIG. 2 vs. the kinematic viscosity of oil samples measured using the system of FIG. 1.

FIG. 3 depicts a plot 300 of the slopes of the fitted lines shown in FIG. 2 (in a.u./s) vs the kinematic viscosity (in centistokes (cSt)) of each sample at 20° C. As shown in FIG. 3, an exponential curve 302 may be fitted to the slope values. The exponential curve 302 has a coefficient of determination of 0.98 or 98%, thus supporting the use of the initial fluorescence rise-time as a measurement of lubrication oil viscosity. The exponential curve 302 may be represented by Equation 2:

$$\ln(Y) = A*X + B \quad (2)$$

Where Y is the rise time in a.u./s, X is the viscosity in cSt, and A and B are fitting parameters. Accordingly, based on Equation 2, the viscosity of a lubrication oil may be determined by Equation 3:

$$\text{Viscosity} = \frac{\ln(Risetime) - B}{A}, \quad (3)$$

Where Risetime is measured in a.u./s and Viscosity is measured in cSt.

Thus, in some embodiments, the viscosity of a lubrication oil for the sample data described above may be determined by Equation 4:

$$\text{Viscosity} = \frac{\ln(Risetime) - 84.58}{-2.66}, \quad (4)$$

It should be appreciated that, in other embodiments, Equation 2 may be modified according to fluorescence rise-time measurements obtained for other types of oil samples. For example, other oil samples having known viscosities may be obtained and measured in the manner described supra to derive an equation similar to Equation 2.

Figure 4:
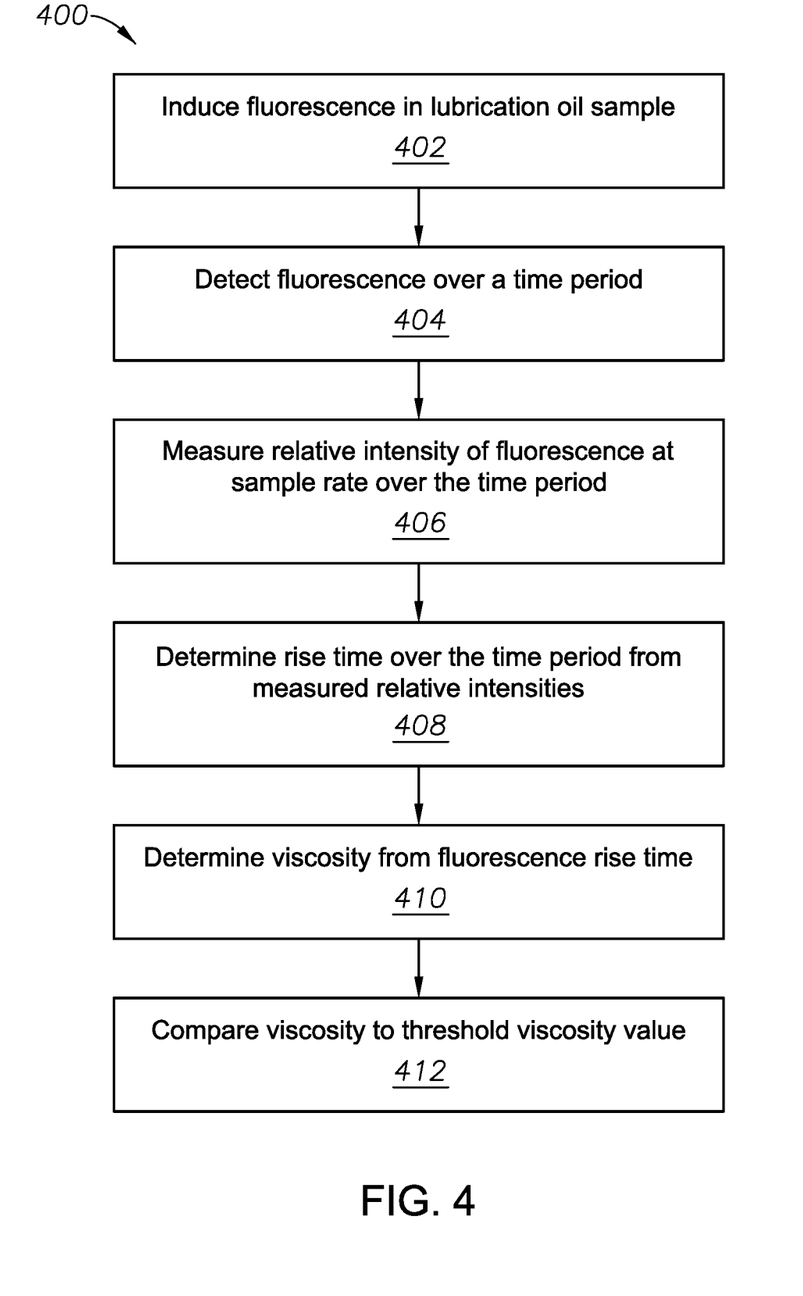
FIG. 4 is a block diagram of a process for determining the viscosity of a lubrication oil sample from the fluorescence rise-time in accordance with an embodiment of the disclosure.
Figure 5A:
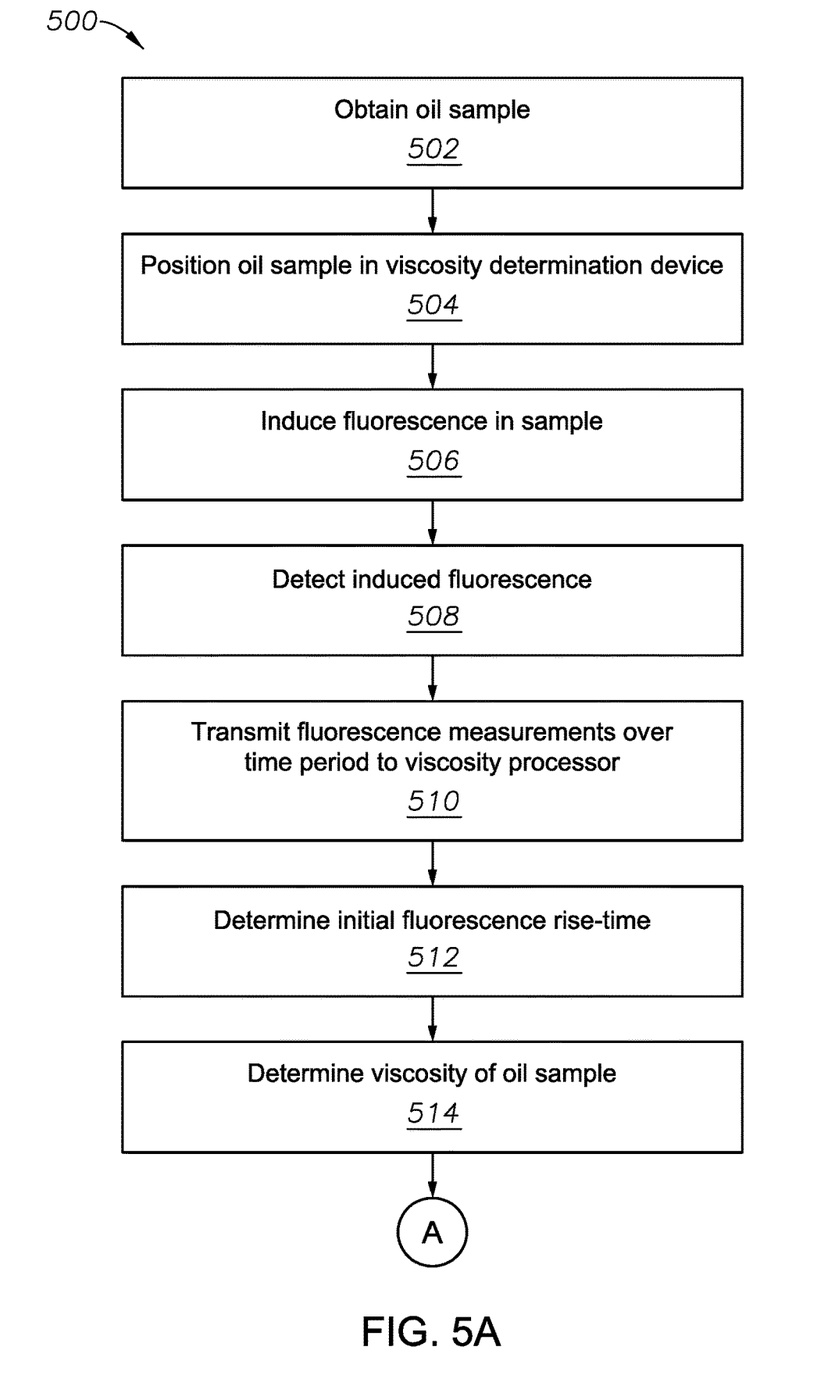
FIGS. 5A and 5B are block diagrams of a process for determining lubrication oil deterioration from fluorescence rise-time of a lubrication oil sample in accordance with an embodiment of the disclosure.
Figure 5B:
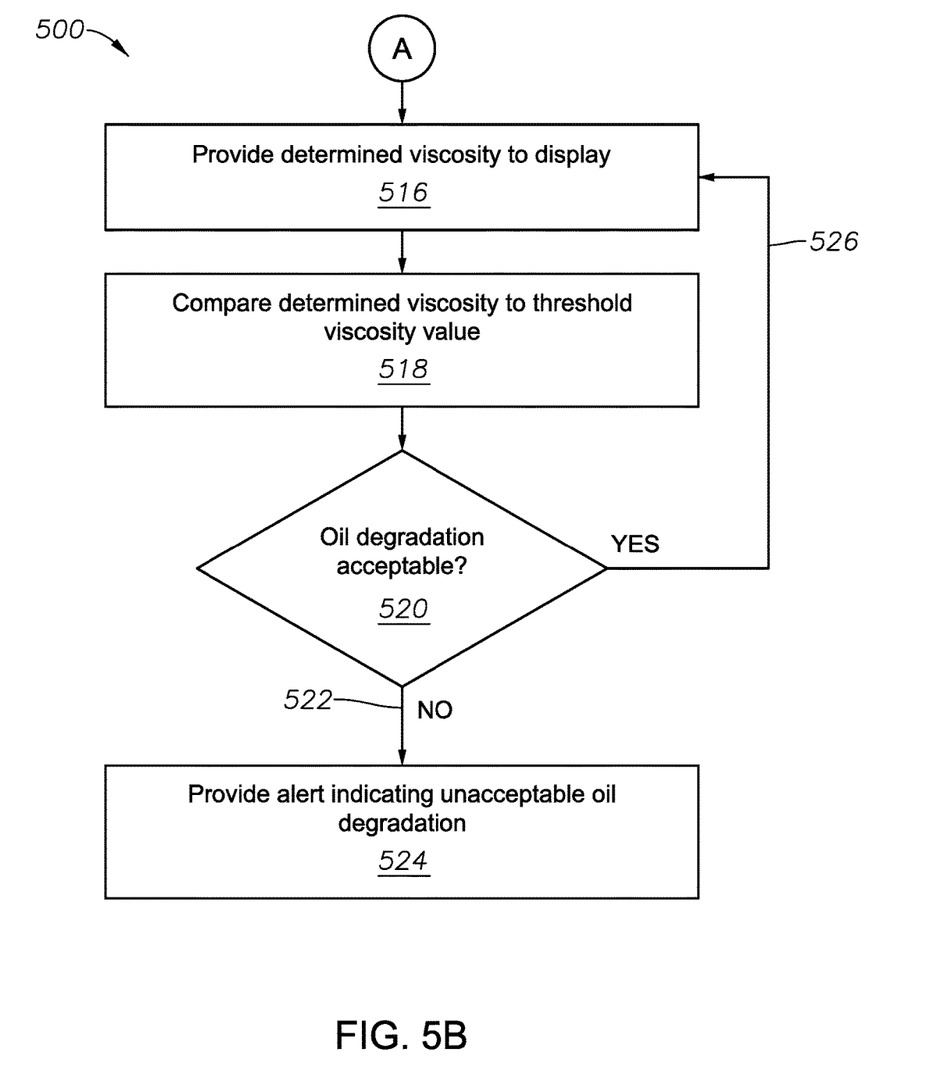
Figure 6:
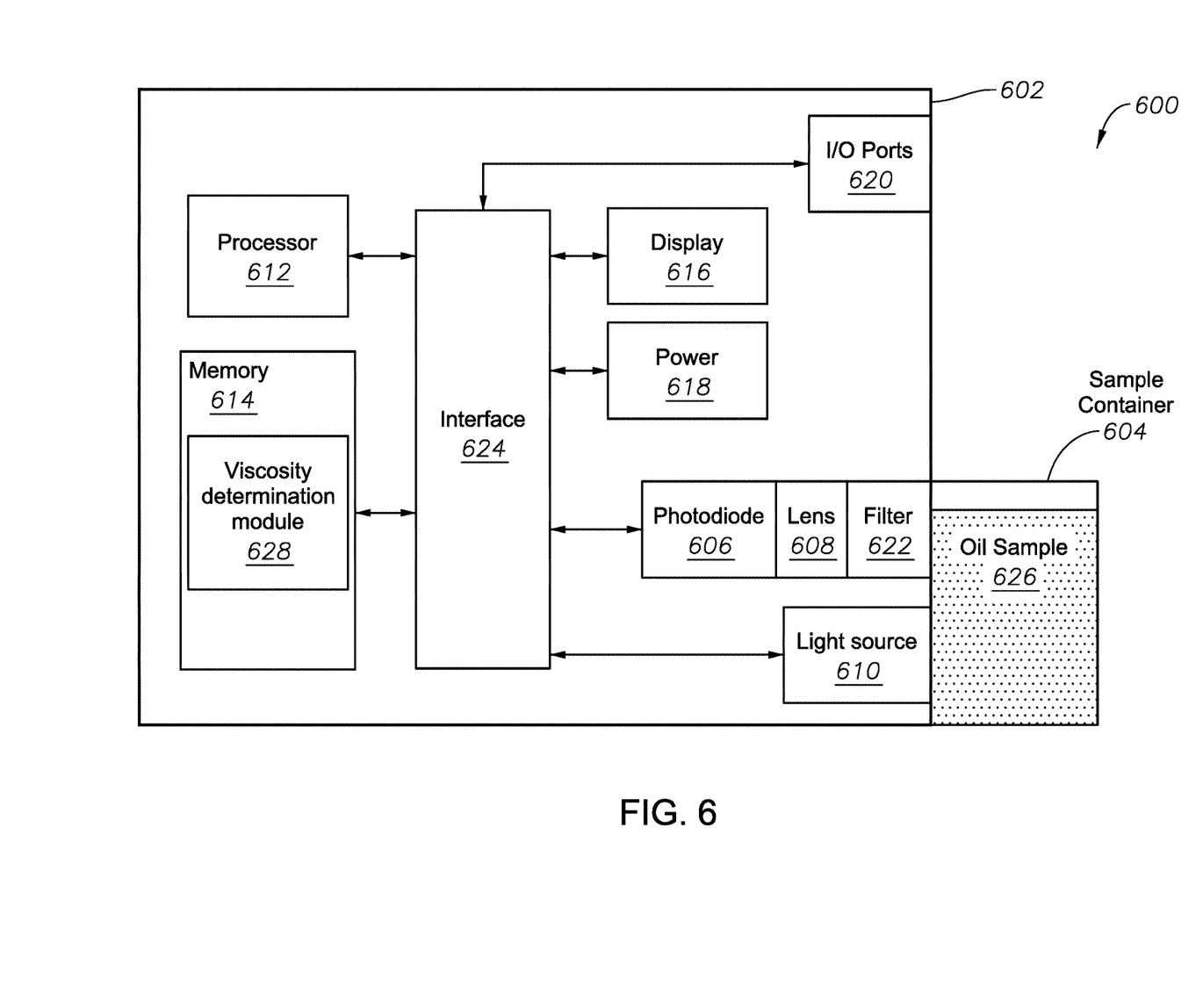
FIG. 6 is a block diagram of a portable viscosity determination device for determining the viscosity of a lubrication oil from fluorescence rise-time in accordance with an embodiment of the disclosure.

As described infra, embodiments of the disclosure may include devices and methods for determining the viscosity of a lubrication oil from the fluorescence rise-time as determined from a sample of the lubrication oil. FIGS. 4 and 5 depict processes for determining the viscosity of a lubrication oil from the fluorescence rise-time of an oil sample in accordance with embodiments of the disclosure. FIG. 6 depicts a portable viscosity determination device in accordance with an embodiment of the disclosure.

Processes for Determining Viscosity and the Deterioration of an Oil

FIG. 4 depicts a process 400 for determining the viscosity of a lubrication oil sample from the fluorescence rise-time in accordance with an embodiment of the disclosure. In some embodiments, some or all portions of the process 400 may be implemented in a system or device for determining the viscosity of a lubrication oil sample from the fluorescence rise-time. In some embodiments, the process 400 may be performed onsite at the location of machine using the lubrication oil. The process 400 may provide for the determination of viscosity in a relatively short amount of time as compared to previous techniques for determining viscosity. For example, in some embodiments the viscosity of a lubrication oil determined using the process 400 may be determined in 30 seconds or less.

Initially, fluorescence may be induced in a lubrication oil sample (block 402). As previously described, in some embodiments fluorescence may be induced using a laser or other light source. The fluorescence may be induced at only one wavelength. Thus the laser or other light source may only provide light at a single wavelength, and the determinations of viscosity may be obtained from a fluorescence signal at only one wavelength. Next, the fluorescence may be detected over a time period (block 404). In some embodiments, the time period may be 5 seconds or greater, 10 seconds or greater, 15 seconds or greater, or 20 seconds or greater. The fluorescence may be detected at intervals over the time period.

Next, the relative intensity of the fluorescence may be measured at intervals (for example, a sample rate) over the time period (block 406). In some embodiments, the interval may be 0.01 seconds or greater, 0.02 seconds or greater, 0.03 seconds or greater, 0.04 seconds or greater, or 0.05 seconds or greater. In some embodiments, the sample rate may be selected based on the fluorescence quantum yield of the sampled oil and the sensitivity of the detector (for example, the photodiode). For example, a detector of relative higher sensitivity may enable a shorter measurement interval (higher sample rate). As previously described, in some embodiments, the fluorescence may be detected using a photodiode and, in some embodiments, may be filtered and collimated before detection by the photodiode.

After detecting the fluorescence emitted from the oil sample, the fluorescence rise-time over the time period may be determined from the measurements (block 408). In some embodiments, a minimum number of measurements may be obtained before determining the fluorescence rise-time. In some embodiments, the fluorescence rise-time may be determined over the entire time period of measurements or for a portion of the time period.

Next, the viscosity of sampled lubrication oil may be determined from the fluorescence rise-time (block 410) using, for example, Equation 2 described supra. In some embodiments, the viscosity may be compared to a threshold viscosity value (block 412) to determine if the viscosity of the sampled lubrication oil deviates from the threshold viscosity value and is indicative of oil deterioration. For example, if the determined viscosity of the sampled lubrication oil is greater than the threshold viscosity value by a specified amount or percentage, the determined viscosity may indicate oil deterioration. In another example, if the determined viscosity of the sampled lubrication oil is less than the threshold viscosity value by a specified amount or percentage, the determined viscosity may indicate oil deterioration.

In some embodiments, the threshold viscosity value may be determined from prior measurement data and viscosity determinations of the sampled lubrication oil. In some embodiments, the threshold viscosity value may be the viscosity of unused lubrication oil having the same or similar composition as the sampled lubrication oil. For example, in some embodiments, a database of known viscosities for lubrication oils, including unused oils and deteriorated oils, may be created and used to obtain threshold viscosity values.

FIGS. 5A and 5B depict a process 500 for determining lubrication oil deterioration from fluorescence rise-time of a lubrication oil sample using, for example, a portable viscosity determination device or a system for determining viscosity from fluorescence rise-time in accordance with an embodiment of the disclosure. As will be appreciated, the viscosity determination from fluorescence rise-time (and, in some embodiments, the use of a portable viscosity determination device for determining the viscosity) may provide a relatively fast assessment of the deterioration condition of lubrication oils, enable early detection of degraded lubrication oil, and provide for an estimation of the remaining lifetime of such lubrication oils. Moreover, such techniques and devices may use a relatively small sample of lubrication oil.

Initially, a sample of lubrication oil may be obtained from a machine (block 502). For example, in some embodiments the lubrication oil sample may be obtained onsite at the location of the machine. For example, in some embodiments a turbine oil may be obtained from a gas turbine at a gas turbine plant. In some embodiments, the volume of the lubrication oil sample may be one milliliter or greater or two milliliters or greater. In some embodiments, multiple lubrication oil samples may be obtained and processed according to process 500. In some embodiments, a lubrication oil sample may be obtained at a first time to establish a baseline fluorescence rise-time or baseline viscosity. In such embodiments, one or more lubrication oil samples may be obtained after the first time and processed in accordance with the techniques described infra. In some embodiments, the lubrication oil sample may be collected in a sample container for a portable viscosity determination device or other suitable sample container.

Next, the lubrication oil sample may be positioned in a viscosity determination device or system (block 504). In some embodiments, for example, a sample container having the lubrication oil sample may be attached to or placed in proximity to a portable viscosity determination device for determining viscosity.

As previously described, fluorescence may be induced in the lubrication oil sample (block 506) using a light source, and the induced fluorescence may be detected (block 508). In some embodiments, for example, a light source of a portable viscosity determination device may emit light into a sample container attached to or in proximity to the portable viscosity determination device to induce fluorescence in a lubrication oil sample in the sample container. In some embodiments, the fluorescence induced in the lubrication oil sample may be detected by a photodiode of the portable viscosity determination device. In some embodiments, as noted supra, the induced fluorescence may be filtered and collimated before detection by a photodiode. As noted supra, in some embodiments the fluorescence may be detected over a time period and at intervals (that is, at a sample rate) over the time period.

Next, the fluorescence measurements may be provided to a viscosity processor (block 510). For example, the viscosity processor may be a processor of a portable viscosity determination device. As previously described, the viscosity processor may determine a fluorescence rise-time from the fluorescence measurements (block 512) and may determine a viscosity of the lubrication oil sample based on the fluorescence rise-time (block 514). As mentioned supra, the light source may only provide light at a single wavelength, and the determination of viscosity of the lubrication oil may be obtained from a fluorescence signal at only one wavelength.

As shown by connector block A, the process 500 is further illustrated in FIG. 5B. As shown in FIG. 5B, in some embodiments the determined viscosity may be provided to a display (block 516). For example, after a viscosity is determined from the fluorescence rise-time of the lubrication oil sample, the viscosity may be provided to a display of a portable viscosity determination device and displayed on the display. Additionally, in some embodiments, the determined viscosity may be compared to a threshold viscosity value (block 518) to determine whether oil deterioration is acceptable (decision block 520). For example, if the determined viscosity of the sampled lubrication oil deviates from (for example, is greater than or lesser than) the threshold viscosity value by a specified amount or percentage, the oil deterioration of the sampled lubrication oil may be determined to be unacceptable.

In some embodiments, if the oil deterioration is determined to be unacceptable (line 522), a notification indicating the oil deterioration may be provided (block 524). In some embodiments, a visual notification (for example, a visual alert or alarm) may be provided on a display of a portable viscosity determination device. In some embodiments, an audio notification (for example, an audio alert or alarm) may additionally or alternatively be provided on an audio output device of a portable viscosity determination device. Thus, in some embodiments, the techniques described in the disclosure may be used to determine an alarm associated with the deterioration of an oil. If the oil deterioration is acceptable (line 526), for example, greater than the threshold value, the viscosity may be provided to a display (block 516) without providing an alert.

In some embodiments, a determined fluorescence rise-time from a sample lubrication oil may be compared to a fluorescence rise-time (for example, a single fluorescence rise-time or an average of fluorescence rise-times) for the same or similar oils. For example, a determined fluorescence rise-time may be compared to determine whether the fluorescence rise-time deviates from a baseline value and is indicative of oil deterioration. In some embodiments, a fluorescence rise-time from a sampled lubrication oil may be compared to fluorescence rise-times determined from previous samples of the lubrication oil from the same machine. For example, a determined fluorescence rise-time may be compared to previous fluorescence rise-times (for example, a single fluorescence rise-time or an average of fluorescence rise-times) to determine whether the fluorescence rise-time deviates from a baseline value and is indicative of oil deterioration.

Portable Viscosity Determination Device

FIG. 6 is a block diagram of a portable viscosity determination device 600 for determining the viscosity of a lubrication oil from fluorescence rise-time in accordance with an embodiment of the disclosure. The portable viscosity determination device 600 may include components disposed in a housing 602 that generally encloses some or all of the components of the device 600. In some embodiments, the device 600 may include a sample container 604, a photodiode 606, a lens 608, a light source 610, one or more processors 612, a memory 614, a display 616, a power source 618, and input/output (I/O) ports 620. In some embodiments, the portable viscosity determination device 600 may also include an optical filter 622. In some embodiments, some or all components of the portable viscosity determination device 600 may communicate via an interface 624 (for example, one or more interfaces). In some embodiments, some components of the portable viscosity determination device 600 may be omitted to decrease the size of the device 600 and increase portability of the device 600. For example, in some embodiments the lens 608, the filter 622, or both may be omitted. In some embodiments, the portable viscosity determination device 600 may be a handheld device such that the housing 602 includes or forms ergonomic features to enable use in one or both hands of an operator.

In some embodiments, the housing 600 may be formed from plastic, metal, or both. The housing 600 may include one or more receptacles for receiving components of the device 600, such as a receptacle for the sample container 604. The housing 600 may include recesses or other features to house components, such as the I/O ports 620, that may provide for connection to external devices. In some embodiments, the housing 600 may include or enclose active cooling components (for example, fans), passive cooling components (for example, heat sinks), for cooling components of the portable viscosity determination device 600.

The sample container 604 may be a glass container or formed from another transparent material. In some embodiments, the sample container 604 may be a cuvette and may have a rectangular shape or other shape. In some embodiments, the housing 600 may have a receptacle or other feature configured to receive the sample container 604. The sample container 604 may contain a sample 626 of lubrication oil for analysis by portable viscosity determination device 600. For example, in some embodiments, the lubrication oil sample 626 may be obtained from a machine and placed in the sample container 604. In some embodiments, the sample container 604 may be removably attached to the housing 600, such that when the sample container 604 is attached the lubrication oil sample 626 may be analyzed by the portable viscosity determination device 600.

The light source 610 may be arranged to emit light into the sample container 610 and excite fluorescence into lubrication oil sample 626 in the manner described supra. In some embodiments, for example, the light source 610 may be a laser similar to the laser 106 described supra. For example, the light source 610 may be a laser having a wavelength of 405 nm, a pulse width of about 5 nanoseconds (ns), and an energy per pulse of about 2 millijoules (mJ). In some embodiments, however, the light source 610 may a wavelength within a range of about 350 nm to about 550 nm. In such embodiments, the wavelength of the light source 610 may be selected based on minimization of the signal-to-noise ratio associated with the induced fluorescence. In some embodiments, parameters of the light source 610 may be selected to minimize power consumption of the portable viscosity determination device 600. In some embodiments, the light source 610 may be removably attached to the housing 602 of the portable viscosity determination device 600 to enable easy repair or replacement of the light source 610. Alternatively, in some embodiments, the portable viscosity determination device 600 may include a light source such a light-emitting diode (LED) instead of the light source 610. In such embodiments, the LED may emit light at the same or similar wavelength as the laser 106 previously described and may other parameters similar to the laser 106.

The optical filter 622 may be a narrow bandpass optical filter and may be a plastic filter or glass filter. The optical filter 622 may be arranged to filter induced fluorescence before transmission to the lens 608. The lens 608 may collimate fluorescence induced in the lubrication oil sample 626, and the collimated fluorescent light may transmit to the photodiode 606. For example, the light source 610, the lens 608, the filter 622, and the photodiode 606 may be arranged to minimize or prevent light emitted from the light source 610 from contacting the lens 608 and the photodiode 606 and to maximize the transmission of the induced fluorescence from the lubrication oil sample 626 to the lens 608 and the photodiode 606. In some embodiments, the light source may be arranged such that light from the light source irradiates the lubrication oil sample at a 45° angle from the surface of the sample container and the photodiode may be arranged at a 90° angle from the surface of the lubrication oil sample. In some embodiments, the lens 608 may be a glass lens and may be integrated into the housing 602 of the portable viscosity determination device 600. The photodiode 606 may provide a digital signal to the viscosity processor 612 via the one of more interfaces 622. In some embodiments, amplifiers or other components may be included to facilitate communication of a digital signal from the photodiode 606.

The viscosity processor 612 (as used the disclosure, the term "processor" encompasses microprocessors) may include one or more processors having the capability to receive signals from the photodiode 606 at a desired rate. In some embodiments, the viscosity processor 612 may include an application-specific integrated circuit (AISC). In some embodiments, the viscosity processor 612 may include a reduced instruction set (RISC) processor. Additionally, the viscosity processor 612 may include a single-core processors and multicore processors and may include graphics processors. Multiple processors may be employed to provide for parallel or sequential execution of one or more of the techniques described in the disclosure. The viscosity processor 612 may receive instructions and data from a memory (for example, memory 614).

The memory 614 (which may include one or more tangible non-transitory computer readable storage medium) may include volatile memory, such as random access memory (RAM), and non-volatile memory, such as ROM, flash memory, a hard drive, any other suitable optical, magnetic, or solid-state storage medium, or a combination thereof. The memory 614 may be accessible by the viscosity processor 612 and, in some embodiments, other components of the portable viscosity determination device 600. The memory 614 may store executable computer code, such as the firmware for the portable viscosity determination device 600, and other executable code. The executable computer code may include computer program instructions for implementing one or more techniques described in the disclosure, For example, the executable computer code may include a viscosity determination module 628 executable by a processor (for example, the viscosity processor 612) to implement one or more embodiments of the present disclosure. In some embodiments, the viscosity determination module 628 may implement one or more elements of process 400 described supra and illustrated in FIG. 4 or process 500 described supra and illustrated in FIGS. 5A and 5B. For example, in some embodiments, the viscosity determination module 628 may receive fluorescence intensity measurements from the photodiode 606 and determine a fluorescence rise-time from the measurements. In some embodiments, the viscosity determination module 628 may determine a viscosity of the oil sample in the sample container from the fluorescence rise-time and may output the determined viscosity for storage in the memory 614 and, in some embodiments, display by the display 616.

As previously mentioned, the memory 614 may include volatile memory, such as random access memory (RAM). The memory 614 may also include non-volatile memory, such as ROM, flash memory, a hard drive, any other suitable optical, magnetic, or solid-state storage medium, or a combination thereof. The interface 624 may include multiple interfaces and may couple various components of the portable viscosity determination device 600 to the viscosity processor 612 and memory 614. In some embodiments, the interface 624, the viscosity processor 612, memory 614, and one or more other components of the portable viscosity determination device 600 may be implemented on a single chip, such as a system-on-a-chip (SOC). In other embodiments, these components, their functionalities, or both may be implemented on separate chips. The interface 624 may be coordinate I/O traffic between processors 612, system memory 614, and other components of the portable viscosity determination device 600. The interface 624 may perform protocol, timing or other data transformations to convert data signals from one component (for example, system memory 614) into a format suitable for use by another component (for example, processors 614). The interface 624 may include support for devices attached through various types of peripheral buses, such as a variant of the Peripheral Component Interconnect (PCI) bus standard or the Universal Serial Bus (USB) standard.

The display 616 may include a liquid crystal display (LCD), an organic light emitting diode (OLED) display, or other suitable display. The display 616 may display a user interface (for example, a graphical user interface), such a user interface for initiating measurement and viscosity determination of a lubrication oil sample in the sample container 604. In accordance with some embodiments, the display 616 may be a touch screen and may include or be provided with touch sensitive elements through which a user may interact with the user interface. In some embodiments, as described in the disclosure, the display 616 may display the status of the measurement and viscosity determination of the lubrication oil sample 626. In some embodiments, the display 616 may display a viscosity determined from the fluorescence rise-time determined from measured induced fluorescence of the oil sample 626. Additionally, in some embodiments, the display 616 may display a notification to a user of the portable viscosity determination device 600. For example, the display 616 may display an alert based on a determination that a viscosity of an oil sample is deviates from a threshold viscosity value.

The power source 618 may include power sources suitable for powering the components of the portable viscosity determination device 600. In some embodiments, the power source 618 may include one or more batteries. In some embodiments, the power source 618 may include an AC to DC converter. In such embodiments, the portable viscosity determination device 600 may be connected to a source of AC (for example, a power grid) via the I/O ports 620. In such embodiments, the power source 618 may provide DC to charge a battery, to power components of the portable viscosity determination device 600, or both. Additionally, in some embodiments the power source 618 may include a first power source for powering a one or more components of the portable viscosity determination device 600 and a second power source for powering a second one or more components of the portable viscosity determination device 600. For example the power source 618 may include a first power source for powering the light source 610 and a second power source for powering the other components of the portable viscosity determination device 600.

The I/O ports 620 may enable the connection of external devices to the portable viscosity determination device 600. Embodiments of the portable viscosity determination device 600 may include any number of I/O ports 620, including headphone and headset jacks, universal serial bus (USB) ports, Firewire or IEEE-1394 ports, AC power connectors, and DC power connectors. Further, portable viscosity determination device 600 may use the input and output ports to connect to and send or receive data with other devices, such as portable computers, desktop computers, printers, etc.

In some embodiments, the portable viscosity determination device 600 may transfer data to other device. For example, in some embodiments the portable viscosity determination device 600 may obtain measurements of fluorescence from the oil sample 626 and transfer the measurements to another device for processing. In some embodiments, the portable viscosity determination device 600 may transfer determined viscosities to another device. In some embodiments the portable viscosity determination device 600 may be connected to another device via the I/O ports 620 and may transfer measurement data, viscosity data, or other data to the device. In some embodiments, the portable viscosity determination device 600 may include a network interface to enable communication with one or more networks. In such embodiments, the portable viscosity determination device 600 may transfer data to another device over one or more networks via the network interface.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used in the disclosure are for organizational purposes only and are not meant to be used to limit the scope of the description.

What is claimed is:

1. A method for determining deterioration of an oil, comprising: determining a fluorescence rise-time of an oil sample from two or more measurements of induced fluorescence in the oil sample, the oil sample comprising a sample of an oil from a machine; determining the viscosity of the oil from the fluorescence rise-time; comparing the viscosity to a viscosity threshold; determining deterioration of the oil based on the comparison, wherein determining the viscosity of the oil from the fluorescence rise-time comprises determining the viscosity according to the following:

$$\text{Viscosity} = \frac{\ln(\text{Risetime}) - B}{A},$$

where A and B are fitting parameters.

2. The method of claim 1, comprising:
emitting light from a light source into the oil sample to induce fluorescence in the oil sample;
measuring, over a time period, the intensity of the detected fluorescence at a sample rate to obtain the two or more measurements.

3. The method of claim 2, wherein the light source comprises a laser.

4. The method of claim 3, wherein the laser emits light comprising a wavelength of 405 nm.

5. The method of claim 2, wherein the sample rate is 20 milliseconds.

6. The method of claim 2, wherein measuring, over a time period, the intensity of the detected fluorescence at a sample rate to obtain the two or more measurements comprises measuring the intensity of the detected fluorescence using a photodiode.

7. The method of claim 2, comprising:
filtering the induced fluorescence before measuring, over a time period, the intensity of the detected fluorescence at a sample rate to obtain the two or more measurements; and
collimating the induced fluorescence before measuring, over a time period, the intensity of the detected fluorescence at a sample rate to obtain the two or more measurements.

8. The method of claim 1, wherein determining deterioration of the oil based on the comparison comprising determining that the oil is deteriorated if the viscosity deviates from the viscosity threshold by a predetermined amount or by a predetermined percentage.

9. The method of claim 8, comprising providing a notification on a display of a viscosity determination device indicating the oil has deteriorated.

10. The method of claim 1, wherein the machine comprise a gas turbine and the oil comprises a gas turbine oil.

11. The method of claim 1, comprising obtaining the oil sample from the machine.

12. The method of claim 11, wherein obtaining the oil sample comprises depositing the oil sample in a glass cuvette.

13. The method of claim 1, comprising providing a notification on a display of a viscosity determination device if the viscosity deviates from the viscosity threshold by a predetermined amount or a predetermined percentage.

14. A non-transitory computer-readable storage medium having executable code stored thereon for determining deterioration of an oil, the executable code comprising a set of instructions that causes a viscosity processor to perform the operations comprising: determining a fluorescence rise-time of an oil sample from two or more measurements of induced fluorescence in the oil sample, the oil sample comprising a sample of an oil from a machine; determining the viscosity of the oil from the fluorescence rise-time; comparing the viscosity to a viscosity threshold; and determining deterioration of the oil based on the comparison wherein determining the viscosity of the oil from the fluorescence rise-time comprises determining the viscosity according to the following:

$$\text{Viscosity} = \frac{\ln(\text{Risetime}) - B}{A},$$

where A and B are fitting parameters.

15. The non-transitory computer-readable medium of claim 14, the operations comprising:
controlling a laser to emit light from a light source into the oil sample to induce fluorescence in the oil sample; and
receiving, over a time period, measurements of the intensity of the detected fluorescence by a detector at a sample rate to obtain the two or more measurements.

16. The non-transitory computer-readable medium of claim 15, wherein the light source comprises a laser.

17. The non-transitory computer-readable medium of claim 16, wherein the laser emits light comprising a wavelength of 405 nm.

18. The non-transitory computer-readable medium of claim 15, wherein the sample rate is 20 milliseconds.

19. The non-transitory computer-readable medium of claim 15, wherein the detector comprises a photodiode.

20. The non-transitory computer-readable medium of claim 14, wherein determining deterioration of the oil based on the comparison comprising determining that the oil is deteriorated if the viscosity deviates from the viscosity threshold by a predetermined amount or by a predetermined percentage.

21. The non-transitory computer-readable medium of claim 20, the operations comprising providing, on a display coupled to the viscosity processor, a notification indicating the oil has deteriorated.

22. The non-transitory computer-readable medium of claim 14, wherein the machine comprise a gas turbine and the oil comprises a turbine lubrication oil.

23. The non-transitory computer-readable medium of claim 14, comprising providing a notification, on a display coupled to the viscosity processor if the viscosity deviates from the viscosity threshold by a predetermined amount or a predetermined percentage.

24. A portable oil deterioration determination device, comprising: a housing; a light source disposed in the housing and arranged to emit light into an oil sample contained in a sample container, the oil sample comprising a sample of an oil from a machine; a viscosity processor disposed in the housing; a non-transitory computer-readable memory disposed in the housing, the memory having executable code stored thereon, the executable code comprising a set of instructions that causes a viscosity processor to perform operations comprising: determining a fluorescence rise-time of the oil sample from two or more measurements of fluorescence induced by the light source in the oil sample; determining the viscosity of the oil from the fluorescence rise-time wherein determining the viscosity of the oil from the fluorescence rise-time comprises determining the viscosity according to the following:

$$\text{Viscosity} = \frac{\ln(Risetime) - B}{A},$$

where A and B are fitting parameters.

25. The portable viscosity determination device of claim 24, the operations comprising:
comparing the viscosity to a viscosity threshold; and
determining deterioration of the oil based on the comparison.

26. The portable viscosity determination device of claim 25, wherein determining deterioration of the oil based on the comparison comprises determining that the oil is deteriorated if the viscosity deviates from the viscosity threshold by a predetermined amount or by a predetermined percentage.

27. The portable viscosity determination device of claim 25, the operations comprising providing, on a display coupled to the viscosity processor, a notification indicating the oil has deteriorated.

28. The portable viscosity determination device of claim 25, the operations comprising providing a notification, on a display coupled to the viscosity processor if the viscosity deviates from the viscosity threshold by a predetermined amount or a predetermined percentage.

29. The portable viscosity determination device of claim 24, comprising a detector arranged to detect the induced fluorescence.

30. The portable viscosity determination device of claim 29, wherein the detector is arranged at a 90° angel from a surface of the sample container.

31. The portable viscosity determination device of claim 29, the operations comprising:

controlling the light source to emit light into the oil sample to induce fluorescence in the oil sample; and
receiving, over a time period, measurements of the intensity of the induced fluorescence by the detector at a sample rate to obtain the two or more measurements.

32. The portable viscosity determination device of claim 31, wherein the sample rate is 20 milliseconds.

33. The portable viscosity determination device of claim 29, wherein the detector comprises a photodiode.

34. The portable viscosity determination device of claim 29, comprising:
a filter disposed in the housing and arranged to filter the induced fluorescence before detection of the induced fluorescence by the detector.

35. The portable viscosity determination device of claim 29, comprising:
a lens disposed in the housing and arranged to collimate the induced fluorescence before detection of the induced fluorescence by the detector.

36. The portable viscosity determination device of claim 24, comprising a power source disposed in the housing and configured to provide power to the light source, the viscosity processor, and the memory.

37. The portable viscosity determination device of claim 24, comprising a display disposed in the housing and coupled to the processor.

38. The portable viscosity determination device of claim 24, wherein the light source is arranged to irradiate the oil sample in the sample container at a 45° angle from a surface of the oil sample.

39. The portable viscosity determination device of claim 24, wherein the light source comprises a laser.

40. The portable viscosity determination device of claim 24, wherein the machine comprise a gas turbine and the oil comprises a gas turbine oil.

41. The portable viscosity determination device of claim 24, comprising the sample container, wherein the sample container is removably attached to the housing.

42. A method for determining the viscosity of an oil, comprising: emitting light from a light source into a sample of the oil to induce fluorescence in the oil sample; measuring, over a time period, the intensity of the induced fluorescence at a sample rate to obtain two or more measurements; determining a fluorescence rise-time of the oil from the two or more measurements of induced fluorescence in the oil sample; and determining the viscosity of the oil from the fluorescence rise-time wherein determining the viscosity of the oil from the fluorescence rise-time comprises determining the viscosity according to the following:

$$\text{Viscosity} = \frac{\ln(Risetime) - B}{A},$$

where A and B are fitting parameters.

43. The method of claim 42, wherein the light source comprises a laser.

44. The method of claim 43, wherein the laser emits light comprising a wavelength of 405 nm.

45. The method of claim 42, wherein the sample rate is 20 milliseconds.

46. The method of claim 42, comprising:
filtering the induced fluorescence before measuring, over a time period, the intensity of the induced fluorescence at a sample rate to obtain two or more measurements; and collimating the induced fluorescence before measuring, over a time period, the intensity of the induced fluorescence at a sample rate to obtain two or more measurements.

47. A non-transitory computer-readable storage medium having executable code stored thereon for determining the viscosity an oil, the executable code comprising a set of instructions that causes a viscosity processor to perform operations comprising: emitting light from a light source into a sample of the oil to induce fluorescence in the oil sample; measuring, over a time period, the intensity of the induced fluorescence at a sample rate to obtain two or more measurements; determining a fluorescence rise-time of the oil from the two or more measurements of induced fluorescence in the oil sample; and determining the viscosity of the oil from the fluorescence rise-time wherein determining the viscosity of the oil from the fluorescence rise-time comprises determining the viscosity according to the following:

$$\text{Viscosity} = \frac{\ln(Risetime) - B}{A},$$

where A and B are fitting parameters.

48. The non-transitory computer-readable storage medium of claim 47, wherein the light source comprises a laser.

49. The non-transitory computer-readable storage medium of claim 48, wherein the laser emits light comprising a wavelength of 405 nm.

50. The non-transitory computer-readable storage medium of claim 47, wherein the sample rate is 20 milliseconds.

51. The non-transitory computer-readable storage medium of claim 47, the operations comprising:
filtering the induced fluorescence before measuring, over a time period, the intensity of the induced fluorescence at a sample rate to obtain two or more measurements; and
collimating the induced fluorescence before measuring, over a time period, the intensity of the induced fluorescence at a sample rate to obtain two or more measurements.

52. A system for determining the viscosity of an oil, comprising: a viscosity processor; a non-transitory computer-readable memory, the memory having executable code stored thereon, the executable code comprising a set of instructions that causes a viscosity processor to perform the following operations: emitting light from a light source into a sample of the oil to induce fluorescence in the oil sample; measuring, over a time period, the intensity of the induced fluorescence at a sample rate to obtain two or more measurements; determining a fluorescence rise-time of the oil from the two or more measurements of induced fluorescence in the oil sample; and determining the viscosity of the oil from the fluorescence rise-time wherein determining the viscosity of the oil from the fluorescence rise-time comprises determining the viscosity according to the following:

$$\text{Viscosity} = \frac{\ln(Risetime) - B}{A},$$

where A and B are fitting parameters.

53. The system of claim 52, wherein the light source comprises a laser.

54. The system of claim 53, wherein the laser emits light comprising a wavelength of 405 nm.

55. The system of claim 52, wherein the sample rate is 20 milliseconds.

56. The system of claim 52, the operations comprising:
filtering the induced fluorescence before measuring, over a time period, the intensity of the induced fluorescence at a sample rate to obtain two or more measurements; and
collimating the induced fluorescence before measuring, over a time period, the intensity of the induced fluorescence at a sample rate to obtain two or more measurements.

* * * * *